United States Patent
Sanchez et al.

(10) Patent No.: US 10,446,271 B2
(45) Date of Patent: Oct. 15, 2019

(54) METHOD FOR PROVIDING HEALTHCARE INDUSTRY OPTIMIZED COGNITIVE INSIGHTS

(71) Applicant: Cognitive Scale, Inc., Austin, TX (US)

(72) Inventors: Matthew Sanchez, Austin, TX (US); Manoj Saxena, Austin, TX (US); Akshay Sabhikhi, Austin, TX (US)

(73) Assignee: COGNITIVE SCALE, INC., Austin, TX (US)

( * ) Notice: Subject to any disclaimer, the term of this patent is extended or adjusted under 35 U.S.C. 154(b) by 914 days.

(21) Appl. No.: 14/629,701

(22) Filed: Feb. 24, 2015

(65) Prior Publication Data

US 2016/0048648 A1 Feb. 18, 2016

Related U.S. Application Data

(60) Provisional application No. 62/037,292, filed on Aug. 14, 2014.

(51) Int. Cl.
*G06N 5/04* (2006.01)
*G16H 50/20* (2018.01)
*G06F 19/00* (2018.01)
*G06N 20/00* (2019.01)

(52) U.S. Cl.
CPC ............. *G16H 50/20* (2018.01); *G06F 19/00* (2013.01); *G06N 5/04* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 9,230,019 B2 | 1/2016 | Koonce et al. | |
| 9,460,392 B2 | 10/2016 | Sanchez | |
| 9,514,418 B2 | 12/2016 | Sanchez | |
| 9,665,825 B2 | 5/2017 | Sanchez | |
| 9,798,977 B2 | 10/2017 | Saxena et al. | |
| 9,798,978 B2 | 10/2017 | Sanchez et al. | |
| 2003/0120681 A1 | 6/2003 | Baclawski | |
| 2008/0033899 A1 | 2/2008 | Barnhill et al. | |
| 2011/0238611 A1 | 9/2011 | McSherry et al. | |
| 2012/0143013 A1 | 6/2012 | Davis, III et al. | |
| 2014/0304395 A1 | 10/2014 | Chandrayana et al. | |
| 2015/0294216 A1 | 10/2015 | Baughman et al. | |
| 2015/0356422 A1 | 12/2015 | Sanchez et al. | |

(Continued)

OTHER PUBLICATIONS

Verheij, et al., Querying and ranking news items in the Hermes framework, Proceedings of the 27th Annual ACM Symposium on Applied Computing, Mar. 26-30, 2012, pp. 672-679.*

(Continued)

*Primary Examiner* — Wilbert L Starks
(74) *Attorney, Agent, or Firm* — Terrile, Cannatti & Chambers; Stephen A. Terrile

(57) ABSTRACT

A method for providing healthcare optimized cognitive insights comprising: receiving data from a plurality of data sources, at least some of the plurality of data sources comprising healthcare relevant data sources; processing the data from the plurality of data sources to provide cognitively processed insights; performing a learning operation to iteratively improve the cognitively processed insights over time; and, providing the cognitively processed healthcare relevant insights to a destination.

13 Claims, 9 Drawing Sheets

(56) References Cited

U.S. PATENT DOCUMENTS

2016/0048762 A1 2/2016 Sanchez et al.
2016/0048763 A1 2/2016 Sanchez et al.

OTHER PUBLICATIONS

Verheij, et al., Querying and ranking news items in the Hermes framework, Proceedings of the 27th Annual ACM Symposium on Applied Computing, Mar. 26-30, 2012, pp. 672-679 (Year: 2012).*
List of Patents or Patent Applications Treated as Related.
Kaur et al., "Empirical Study on Applications of Data Mining Techniques in Healthcare," Journal of Computer Science 2.2 (2006), 194-200.
Chawla et al., "Bringing Big Data to Personalized Healthcare: A Patient-Center Framework," Journal of General Internal Medicine 28.3 (2013), 660-665.
Demner-Fushman et al., "What Can Natural Language Processing do for Clinical Decision Support?," Journal of Biomedical Informatics 42.5 (2009), 760-772.
Cambria et al., "Sentic PROMs: Application of Sentic Computing to the Development of a Novel Unified Framework for Measuring Health-Care Quality," Expert Systems with Applications 39.12 (2012), 10533-10543.
Zhou et al., "Temporal Reasoning with Medical Data—A Review with Emphasis on Medical Natural Language Processing," Journal of Biomedical Informatics 40.2 (2007), 183-202.
Kawamoto et al., "The HL7-OMG Heathcare Services Specification Project: Motivation, Methodology, and Deliverables for Enabling a Semantically Interoperable Service-Oriented Architecture for Healthcare," Journal of the American Medical Informatics Association 16.6 (2009), 874-881.
Brinal Colaco et al., Privacy Preserving Data Mining for Social Networks, 2014 IEEE International Conference on Advances in Communication and Computing Technologies (ICACACT 2014), pp. 1-4.
Anand D. Sarwate et al., Signal Processing and Machine Learning with Differential Privacy: Algorithms and Challenges for Continuous Data, IEEE Signal Processing Magazine, Sep. 2013, vol. 30, Issue 5, pp. 86-94.
M. Amin Rahimian et al., Group Decision Making and Social Learning, 2016 IEEE 55th Conference on Decision and Control (CDC), Dec. 12-14, 2016, pp. 6783-6794.
Daniela De Venuto et al., Brain-Computer Interface Using P300: A Gaming Approach for Neurocognitive Impairment Diagnosis, 2016 IEEE International Level Design Validation and Test Workshop (HLDVT), 2016, pp. 93-99.
Meng Sun et al., Toward Information Privacy for the Internet of Things: A Nonparametric Learning Approach, IEEE Transactions on Signal Processing, Apr. 1, 2018, vol. 66, No. 7, pp. 1734-1747.
A. Praveena et al., Prevention of Inference Attacks for Private Information in Social Networking Sites, IEEE International Conference on Inventive Systems and Control (ICISC), 2017, pp. 1-7.
Ryan Wooten et al., Design and Implementation of a Secure Healthcare Social Cloud System, Proceedings of the 2012 12th IEEE/ACM International Symposium on Cluster, Cloud and Grid Computing (ccgrid 2012), IEEE Computer Society 2012.

* cited by examiner

METHOD FOR PROVIDING HEALTHCARE INDUSTRY OPTIMIZED COGNITIVE INSIGHTS

BACKGROUND OF THE INVENTION

Field of the Invention

The present invention relates in general to the field of computers and similar technologies, and in particular to software utilized in this field. Still more particularly, it relates to a method, system and computer-usable medium for performing cognitive inference and learning operations.

Description of the Related Art

In general, "big data" refers to a collection of datasets so large and complex that they become difficult to process using typical database management tools and traditional data processing approaches. These datasets can originate from a wide variety of sources, including computer systems, mobile devices, credit card transactions, television broadcasts, and medical equipment, as well as infrastructures associated with cities, sensor-equipped buildings and factories, and transportation systems. Challenges commonly associated with big data, which may be a combination of structured, unstructured, and semi-structured data, include its capture, curation, storage, search, sharing, analysis and visualization. In combination, these challenges make it difficult to efficiently process large quantities of data within tolerable time intervals.

Nonetheless, big data analytics hold the promise of extracting insights by uncovering difficult-to-discover patterns and connections, as well as providing assistance in making complex decisions by analyzing different and potentially conflicting options. As such, individuals and organizations alike can be provided new opportunities to innovate, compete, and capture value.

One aspect of big data is "dark data," which generally refers to data that is either not collected, neglected, or underutilized. Examples of data that is not currently being collected includes location data prior to the emergence of companies such as Foursquare or social data prior to the advent companies such as Facebook. An example of data that is being collected, but is difficult to access at the right time and place, includes data associated with the side effects of certain spider bites while on a camping trip. As another example, data that is collected and available, but has not yet been productized of fully utilized, may include disease insights from population-wide healthcare records and social media feeds. As a result, a case can be made that dark data may in fact be of higher value than big data in general, especially as it can likely provide actionable insights when it is combined with readily-available data.

SUMMARY OF THE INVENTION

In one embodiment, the invention relates to a method for providing healthcare optimized cognitive insights comprising: receiving data from a plurality of data sources, at least some of the plurality of data sources comprising healthcare relevant data sources; processing the data from the plurality of data sources to provide cognitively processed insights; performing a learning operation to iteratively improve the cognitively processed insights over time; and, providing the cognitively processed healthcare relevant insights to a destination.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

DETAILED DESCRIPTION

Figure 1:
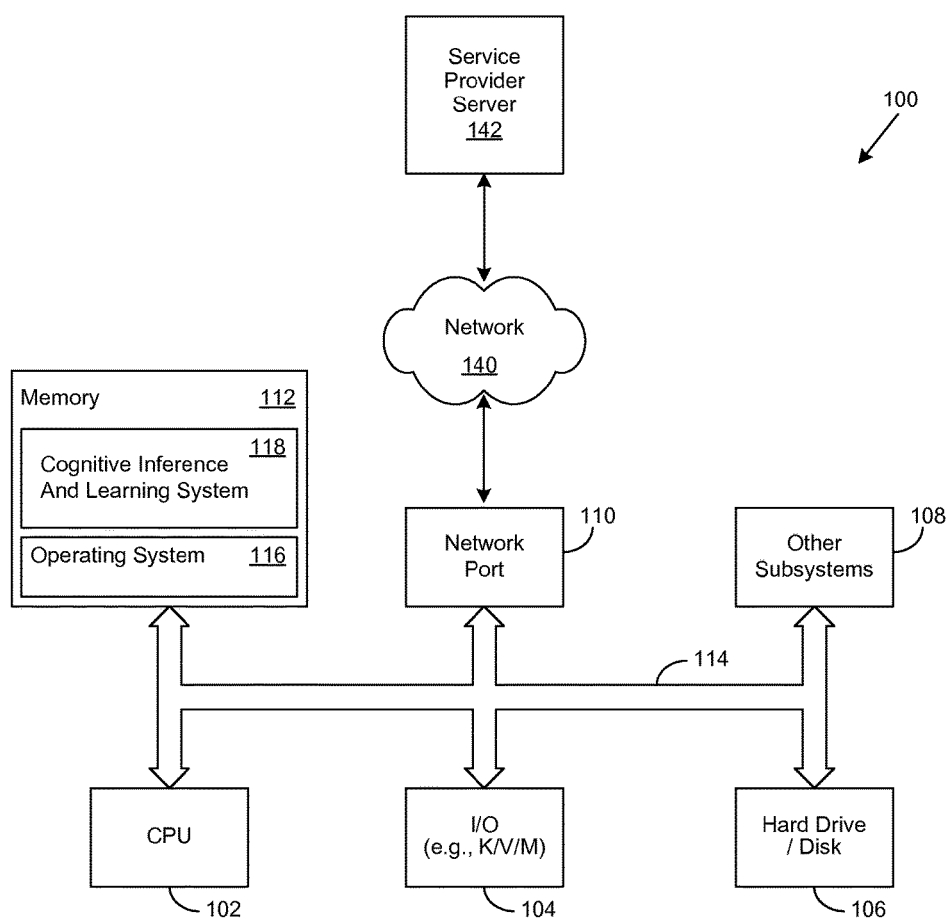
FIG. 1 depicts an exemplary client computer in which the present invention may be implemented.

A method, system and computer-usable medium are disclosed for cognitive inference and learning operations. The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

FIG. 1 is a generalized illustration of an information processing system 100 that can be used to implement the system and method of the present invention. The information processing system 100 includes a processor (e.g., central processor unit or "CPU") 102, input/output (I/O) devices 104, such as a display, a keyboard, a mouse, and associated controllers, a hard drive or disk storage 106, and various other subsystems 108. In various embodiments, the information processing system 100 also includes network port 110 operable to connect to a network 140, which is likewise accessible by a service provider server 142. The information processing system 100 likewise includes system memory 112, which is interconnected to the foregoing via one or more buses 114. System memory 112 further comprises operating system (OS) 116 and in various embodiments may also comprise cognitive inference and learning system (CILS) 118. In these and other embodiments, the CILS 118 may likewise comprise invention modules 120. In one embodiment, the information processing system 100 is able to download the CILS 118 from the service provider server 142. In another embodiment, the CILS 118 is provided as a service from the service provider server 142.

In various embodiments, the CILS 118 is implemented to perform various cognitive computing operations described in greater detail herein. As used herein, cognitive computing broadly refers to a class of computing involving self-learning systems that use techniques such as spatial navigation, machine vision, and pattern recognition to increasingly mimic the way the human brain works. To be more specific, earlier approaches to computing typically solved problems by executing a set of instructions codified within software. In contrast, cognitive computing approaches are data-driven, sense-making, insight-extracting, problem-solving systems that have more in common with the structure of the human brain than with the architecture of contemporary, instruction-driven computers.

To further differentiate these distinctions, traditional computers must first be programmed by humans to perform specific tasks, while cognitive systems learn from their interactions with data and humans alike, and in a sense, program themselves to perform new tasks. To summarize the difference between the two, traditional computers are designed to calculate rapidly. Cognitive systems are designed to quickly draw inferences from data and gain new knowledge.

Cognitive systems achieve these abilities by combining various aspects of artificial intelligence, natural language processing, dynamic learning, and hypothesis generation to render vast quantities of intelligible data to assist humans in making better decisions. As such, cognitive systems can be characterized as having the ability to interact naturally with people to extend what either humans, or machines, could do on their own. Furthermore, they are typically able to process natural language, multi-structured data, and experience much in the same way as humans. Moreover, they are also typically able to learn a knowledge domain based upon the best available data and get better, and more immersive, over time.

It will be appreciated that more data is currently being produced every day than was recently produced by human beings from the beginning of recorded time. Deep within this ever-growing mass of data is a class of data known as "dark data," which includes neglected information, ambient signals, and insights that can assist organizations and individuals in augmenting their intelligence and deliver actionable insights through the implementation of cognitive applications. As used herein, cognitive applications, or "cognitive apps," broadly refer to cloud-based, big data interpretive applications that learn from user engagement and data interactions. Such cognitive applications extract patterns and insights from dark data sources that are currently almost completely opaque. Examples of such dark data include disease insights from population-wide healthcare records and social media feeds, or from new sources of information, such as sensors monitoring pollution in delicate marine environments.

Over time, it is anticipated that cognitive applications will fundamentally change the ways in which many organizations operate as they invert current issues associated with data volume and variety to enable a smart, interactive data supply chain. Ultimately, cognitive applications hold the promise of receiving a user query and immediately providing a data-driven answer from a masked data supply chain in response. As they evolve, it is likewise anticipated that cognitive applications may enable a new class of "sixth sense" applications that intelligently detect and learn from relevant data and events to offer insights, predictions and advice rather than wait for commands. Just as web and mobile applications changed the way people access data, cognitive applications may change the way people listen to, and become empowered by, multi-structured data such as emails, social media feeds, doctors notes, transaction records, and call logs.

However, the evolution of such cognitive applications has associated challenges, such as how to detect events, ideas, images, and other content that may be of interest. For example, assuming that the role and preferences of a given user are known, how is the most relevant information discovered, prioritized, and summarized from large streams of multi-structured data such as news feeds, blogs, social media, structured data, and various knowledge bases? To further the example, what can a healthcare executive be told about their competitor's market share? Other challenges include the creation of a contextually-appropriate visual summary of responses to questions or queries.

Figure 2:
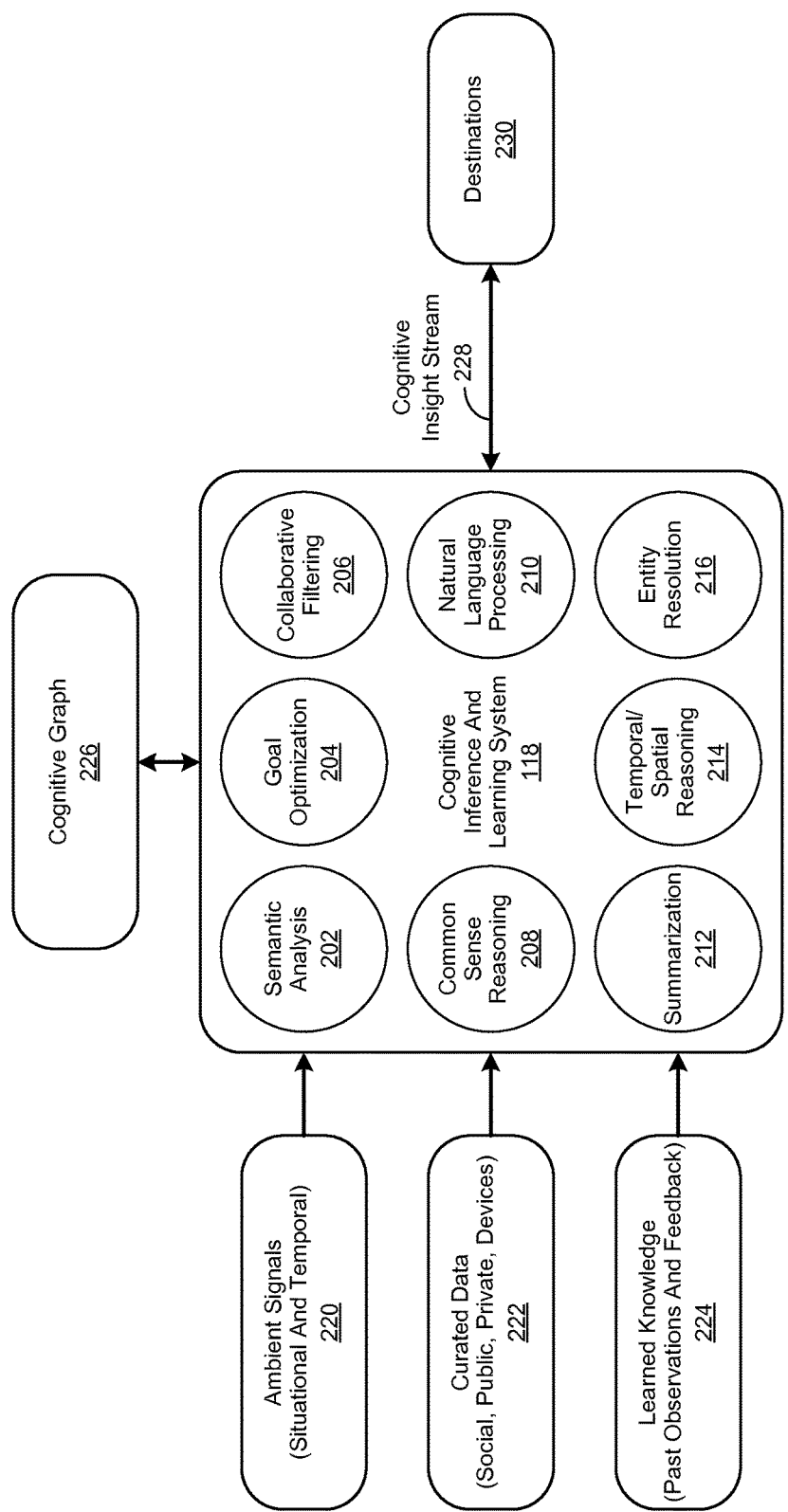
FIG. 2 is a simplified block diagram of a cognitive inference and learning system (CILS)

FIG. 2 is a simplified block diagram of a cognitive inference and learning system (CILS) implemented in accordance with an embodiment of the invention. In various embodiments, the CILS 118 is implemented to incorporate a variety of processes, including semantic analysis 202, goal optimization 204, collaborative filtering 206, common sense reasoning 208, natural language processing 210, summarization 212, temporal/spatial reasoning 214, and entity resolution 216 to generate cognitive insights.

As used herein, semantic analysis 202 broadly refers to performing various analysis operations to achieve a semantic level of understanding about language by relating syntactic structures. In various embodiments, various syntactic structures are related from the levels of phrases, clauses, sentences and paragraphs, to the level of the body of content as a whole and to its language-independent meaning In certain embodiments, the semantic analysis 202 process includes processing a target sentence to parse it into its individual parts of speech, tag sentence elements that are related to predetermined items of interest, identify dependencies between individual words, and perform co-reference resolution. For example, if a sentence states that the author really likes the hamburgers served by a particular restaurant, then the name of the "particular restaurant" is co-referenced to "hamburgers."

As likewise used herein, goal optimization 204 broadly refers to performing multi-criteria decision making operations to achieve a given goal or target objective. In various embodiments, one or more goal optimization 204 processes are implemented by the CILS 118 to define predetermined goals, which in turn contribute to the generation of a cognitive insight. For example, goals for planning a vacation trip may include low cost (e.g., transportation and accommodations), location (e.g., by the beach), and speed (e.g., short travel time). In this example, it will be appreciated that certain goals may be in conflict with another. As a result, a cognitive insight provided by the CILS 118 to a traveler may indicate that hotel accommodations by a beach may cost more than they care to spend.

Collaborative filtering 206, as used herein, broadly refers to the process of filtering for information or patterns through the collaborative involvement of multiple agents, viewpoints, data sources, and so forth. The application of such collaborative filtering 206 processes typically involves very large and different kinds of data sets, including sensing and monitoring data, financial data, and user data of various kinds Collaborative filtering 206 may also refer to the process of making automatic predictions associated with predetermined interests of a user by collecting preferences or other information from many users. For example, if person 'A' has the same opinion as a person 'B' for a given issue 'x', then an assertion can be made that person 'A' is more likely to have the same opinion as person 'B' opinion on a different issue 'y' than to have the same opinion on issue 'y' as a randomly chosen person. In various embodiments, the collaborative filtering 206 process is implemented with various recommendation engines familiar to those of skill in the art to make recommendations.

As used herein, common sense reasoning 208 broadly refers to simulating the human ability to make deductions from common facts they inherently know. Such deductions may be made from inherent knowledge about the physical properties, purpose, intentions and possible behavior of ordinary things, such as people, animals, objects, devices, and so on. In various embodiments, common sense reasoning 208 processes are implemented to assist the CILS 118 in understanding and disambiguating words within a predetermined context. In certain embodiments, the common sense reasoning 208 processes are implemented to allow the CILS 118 to generate text or phrases related to a target word or phrase to perform deeper searches for the same terms. It will be appreciated that if the context of a word is better understood, then a common sense understanding of the word can then be used to assist in finding better or more accurate information. In certain embodiments, this better or more accurate understanding of the context of a word, and its related information, allows the CILS 118 to make more accurate deductions, which are in turn used to generate cognitive insights.

As likewise used herein, natural language processing (NLP) 210 broadly refers to interactions with a system, such as the CILS 118, through the use of human, or natural, languages. In various embodiments, various NLP 210 processes are implemented by the CILS 118 to achieve natural language understanding, which enables it to not only derive meaning from human or natural language input, but to also generate natural language output.

Summarization 212, as used herein, broadly refers to processing a set of information, organizing and ranking it, and then generating a corresponding summary. As an example, a news article may be processed to identify its primary topic and associated observations, which are then extracted, ranked, and then presented to the user. As another example, page ranking operations may be performed on the same news article to identify individual sentences, rank them, order them, and determine which of the sentences are most impactful in describing the article and its content. As yet another example, a structured data record, such as a patient's electronic medical record (EMR), may be processed using the summarization 212 process to generate sentences and phrases that describes the content of the EMR. In various embodiments, various summarization 212 processes are implemented by the CILS 118 to generate summarizations of content streams, which are in turn used to generate cognitive insights.

As used herein, temporal/spatial reasoning 214 broadly refers to reasoning based upon qualitative abstractions of temporal and spatial aspects of common sense knowledge, described in greater detail herein. For example, it is not uncommon for a predetermined set of data to change over time. Likewise, other attributes, such as its associated metadata, may likewise change over time. As a result, these changes may affect the context of the data. To further the example, the context of asking someone what they believe they should be doing at 3:00 in the afternoon during the workday while they are at work may be quite different that asking the same user the same question at 3:00 on a Sunday afternoon when they are at home. In various embodiments, various temporal/spatial reasoning 214 processes are implemented by the CILS 118 to determine the context of queries, and associated data, which are in turn used to generate cognitive insights.

As likewise used herein, entity resolution 216 broadly refers to the process of finding elements in a set of data that refer to the same entity across different data sources (e.g., structured, non-structured, streams, devices, etc.), where the target entity does not share a common identifier. In various embodiments, the entity resolution 216 process is implemented by the CILS 118 to identify significant nouns, adjectives, phrases or sentence elements that represent various predetermined entities within one or more domains. From the foregoing, it will be appreciated that the implementation of one or more of the semantic analysis 202, goal optimization 204, collaborative filtering 206, common sense reasoning 208, natural language processing 210, summarization 212, temporal/spatial reasoning 214, and entity resolution 216 processes by the CILS 118 can facilitate the generation of a semantic, cognitive model.

In various embodiments, the CILS 118 receives ambient signals 220, curated data 222, and learned knowledge, which is then processed by the CILS 118 to generate one or more cognitive graphs 226. In turn, the one or more cognitive graphs 226 are further used by the CILS 118 to generate cognitive insight streams, which are then delivered to one or more destinations 230, as described in greater detail herein.

As used herein, ambient signals 220 broadly refer to input signals, or other data streams, that may contain data providing additional insight or context to the curated data 222 and learned knowledge 224 received by the CILS 118. For example, ambient signals may allow the CILS 118 to understand that a user is currently using their mobile device, at location 'x', at time 'y', doing activity 'z'. To further the example, there is a difference between the user using their mobile device while they are on an airplane versus using their mobile device after landing at an airport and walking between one terminal and another. To extend the example even further, ambient signals may add additional context, such as the user is in the middle of a three leg trip and has two hours before their next flight. Further, they may be in terminal A1, but their next flight is out of C1, it is lunchtime, and they want to know the best place to eat. Given the available time the user has, their current location, restaurants that are proximate to their predicted route, and other factors such as food preferences, the CILS 118 can perform various cognitive operations and provide a recommendation for where the user can eat.

In various embodiments, the curated data 222 may include structured, unstructured, social, public, private, streaming, device or other types of data described in greater detail herein. In certain embodiments, the learned knowledge 224 is based upon past observations and feedback from the presentation of prior cognitive insight streams and recommendations. In various embodiments, the learned knowledge 224 is provided via a feedback look that provides the learned knowledge 224 in the form of a learning stream of data.

As likewise used herein, a cognitive graph 226 refers to a representation of expert knowledge, associated with individuals and groups over a period of time, to depict relationships between people, places, and things using words, ideas, audio and images. As such, it is a machine-readable formalism for knowledge representation that provides a common framework allowing data and knowledge to be shared and reused across user, application, organization, and community boundaries.

In various embodiments, the information contained in, and referenced by, a cognitive graph 226 is derived from many sources (e.g., public, private, social, device), such as curated data 222. In certain of these embodiments, the cognitive graph 226 assists in the identification and organization of information associated with how people, places and things are related to one other. In various embodiments, the cognitive graph 226 enables automated agents, described in greater detail herein, to access the Web more intelligently, enumerate inferences through utilization of curated, structured data 222, and provide answers to questions by serving as a computational knowledge engine.

In certain embodiments, the cognitive graph 226 not only elicits and maps expert knowledge by deriving associations from data, it also renders higher level insights and accounts for knowledge creation through collaborative knowledge modeling. In various embodiments, the cognitive graph 226 is a machine-readable, declarative memory system that stores and learns both episodic memory (e.g., specific personal experiences associated with an individual or entity), and semantic memory, which stores factual information (e.g., geo location of an airport or restaurant).

For example, the cognitive graph 226 may know that a given airport is a place, and that there is a list of related places such as hotels, restaurants and departure gates. Furthermore, the cognitive graph 226 may know that people such as business travelers, families and college students use the airport to board flights from various carriers, eat at various restaurants, or shop at certain retail stores. The cognitive graph 226 may also have knowledge about the key attributes from various retail rating sites that travelers have used to describe the food and their experience at various venues in the airport over the past six months.

In certain embodiments, the cognitive insight stream 228 is bidirectional, and supports flows of information both too and from destinations 230. In these embodiments, the first flow is generated in response to receiving a query, and subsequently delivered to one or more destinations 230. The second flow is generated in response to detecting information about a user of one or more of the destinations 230. Such use results in the provision of information to the CILS 118. In response, the CILS 118 processes that information, in the context of what it knows about the user, and provides additional information to the user, such as a recommendation. In various embodiments, the cognitive insight stream 228 is configured to be provided in a "push" stream configuration familiar to those of skill in the art. In certain embodiments, the cognitive insight stream 228 is implemented to use natural language approaches familiar to skilled practitioners of the art to support interactions with a user.

In various embodiments, the cognitive insight stream 228 may include a stream of visualized insights. As used herein, visualized insights broadly refers to cognitive insights that are presented in a visual manner, such as a map, an infographic, images, and so forth. In certain embodiments, these visualized insights may include various cognitive insights, such as "What happened?", "What do I know about it?", "What is likely to happen next?", or "What should I do about it?" In these embodiments, the cognitive insight stream is generated by various cognitive agents, which are applied to various sources, datasets, and cognitive graphs. As used herein, a cognitive agent broadly refers to a computer program that performs a task with minimum specific directions from users and learns from each interaction with data and human users.

In various embodiments, the CILS 118 delivers Cognition as a Service (CaaS). As such, it provides a cloud-based development and execution platform that allow various cognitive applications and services to function more intelligently and intuitively. In certain embodiments, cognitive applications powered by the CILS 118 are able to think and interact with users as intelligent virtual assistants. As a result, users are able to interact with such cognitive applications by asking them questions and giving them commands. In response, these cognitive applications will be able to assist the user in completing tasks and managing their work more efficiently.

In these and other embodiments, the CILS 118 can operate as an analytics platform to process big data, and dark data as well, to provide data analytics through a public, private or hybrid cloud environment. As used herein, cloud analytics broadly refers to a service model wherein data sources, data models, processing applications, computing power, analytic models, and sharing or storage of results are implemented within a cloud environment to perform one or more aspects of analytics.

In various embodiments, users submit queries and computation requests in a natural language format to the CILS 118. In response, they are provided with a ranked list of relevant answers and aggregated information with useful links and pertinent visualizations through a graphical representation. In these embodiments, the cognitive graph 226 generates semantic and temporal maps to reflect the organization of unstructured data and to facilitate meaningful learning from potentially millions of lines of text, much in the same way as arbitrary syllables strung together create meaning through the concept of language.

Figure 3:
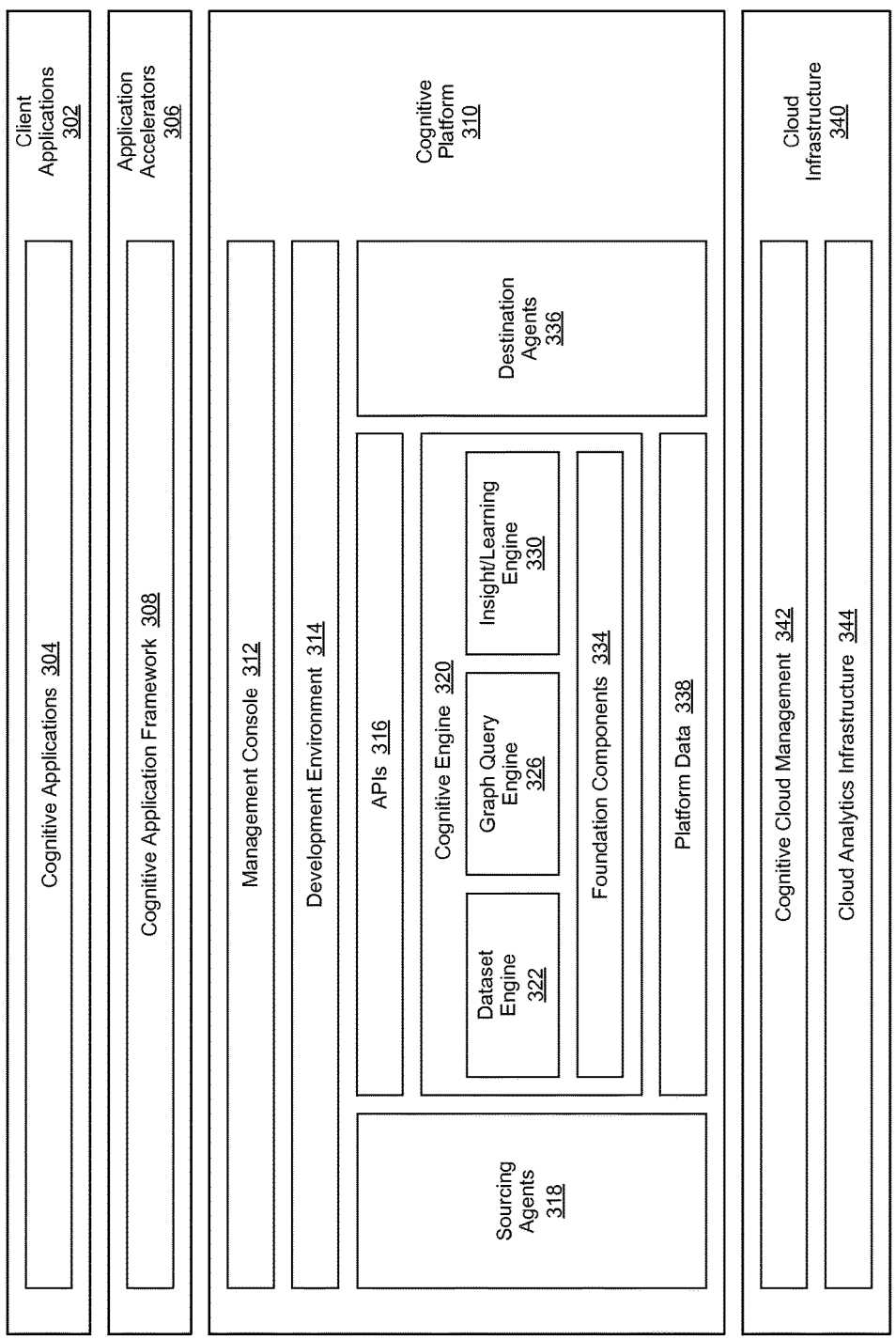
FIG. 3 is a simplified block diagram of a CILS reference model implemented in accordance with an embodiment of the invention.

FIG. 3 is a simplified block diagram of a cognitive inference and learning system (CILS) reference model implemented in accordance with an embodiment of the invention. In this embodiment, the CILS reference model is associated with the CILS 118 shown in FIG. 2. As shown in FIG. 3, the CILS 118 includes client applications 302, application accelerators 306, a cognitive platform 310, and cloud infrastructure 340. In various embodiments, the client applications 302 include cognitive applications 304, which are implemented to understand and adapt to the user, not the other way around, by natively accepting and understanding human forms of communication, such as natural language text, audio, images, video, and so forth.

In these and other embodiments, the cognitive applications 304 possess situational and temporal awareness based upon ambient signals from users and data, which facilitates understanding the user's intent, content, context and meaning to drive goal-driven dialogs and outcomes. Further, they are designed to gain knowledge over time from a wide variety of structured, non-structured, and device data sources, continuously interpreting and autonomously reprogramming themselves to better understand a given domain. As such, they are well-suited to support human decision making, by proactively providing trusted advice, offers and recommendations while respecting user privacy and permissions.

In various embodiments, the application accelerators 306 include a cognitive application framework 308. In certain embodiments, the application accelerators 306 and the cognitive application framework 308 support various plug-ins and components that facilitate the creation of client applications 302 and cognitive applications 304. In various embodiments, the application accelerators 306 include widgets, user interface (UI) components, reports, charts, and back-end integration components familiar to those of skill in the art.

As likewise shown in FIG. 3, the cognitive platform 310 includes a management console 312, a development environment 314, application program interfaces (APIs) 316, sourcing agents 318, a cognitive engine 320, destination agents 336, and platform data 338, all of which are described in greater detail herein. In various embodiments, the management console 312 is implemented to manage accounts and projects, along with user-specific metadata that is used to drive processes and operations within the cognitive platform 310 for a predetermined project.

In certain embodiments, the development environment 314 is implemented to create custom extensions to the CILS 118 shown in FIG. 2. In various embodiments, the development environment 314 is implemented for the development of a custom application, which may subsequently be deployed in a public, private or hybrid cloud environment. In certain embodiments, the development environment 314 is implemented for the development of a custom sourcing agent, a custom bridging agent, a custom destination agent, or various analytics applications or extensions.

In various embodiments, the APIs 316 are implemented to build and manage predetermined cognitive applications 304, described in greater detail herein, which are then executed on the cognitive platform 310 to generate cognitive insights. Likewise, the sourcing agents 318 are implemented in various embodiments to source a variety of multi-site, multi-structured source streams of data described in greater detail herein. In various embodiments, the cognitive engine 320 includes a dataset engine 322, a graph query engine 326, an insight/learning engine 330, and foundation components 334. In certain embodiments, the dataset engine 322 is implemented to establish and maintain a dynamic data ingestion and enrichment pipeline. In these and other embodiments, the dataset engine 322 may be implemented to orchestrate one or more sourcing agents 318 to source data. Once the data is sourced, the data set engine 322 performs data enriching and other data processing operations, described in greater detail herein, and generates one or more sub-graphs that are subsequently incorporated into a target cognitive graph.

In various embodiments, the graph query engine 326 is implemented to receive and process queries such that they can be bridged into a cognitive graph, as described in greater detail herein, through the use of a bridging agent. In certain embodiments, the graph query engine 326 performs various natural language processing (NLP), familiar to skilled practitioners of the art, to process the queries. In various embodiments, the insight/learning engine 330 is implemented to encapsulate a predetermined algorithm, which is then applied to a cognitive graph to generate a result, such as a cognitive insight or a recommendation. In certain embodiments, one or more such algorithms may contribute to answering a specific question and provide additional cognitive insights or recommendations. In various embodiments, two or more of the dataset engine 322, the graph query engine 326, and the insight/learning engine 330 may be implemented to operate collaboratively to generate a cognitive insight or recommendation. In certain embodiments, one or more of the dataset engine 322, the graph query engine 326, and the insight/learning engine 330 may operate autonomously to generate a cognitive insight or recommendation.

The foundation components 334 shown in FIG. 3 include various reusable components, familiar to those of skill in the art, which are used in various embodiments to enable the dataset engine 322, the graph query engine 326, and the insight/learning engine 330 to perform their respective operations and processes. Examples of such foundation components 334 include natural language processing (NLP) components and core algorithms, such as cognitive algorithms.

In various embodiments, the platform data 338 includes various data repositories, described in greater detail herein, that are accessed by the cognitive platform 310 to generate cognitive insights. In various embodiments, the destination agents 336 are implemented to publish cognitive insights to a consumer of cognitive insight data. Examples of such consumers of cognitive insight data include target databases, business intelligence applications, and mobile applications. It will be appreciated that many such examples of cognitive insight data consumers are possible and the foregoing is not intended to limit the spirit, scope or intent of the invention. In various embodiments, as described in greater detail herein, the cloud infrastructure 340 includes cognitive cloud management 342 components and cloud analytics infrastructure components 344.

Figure 4A:
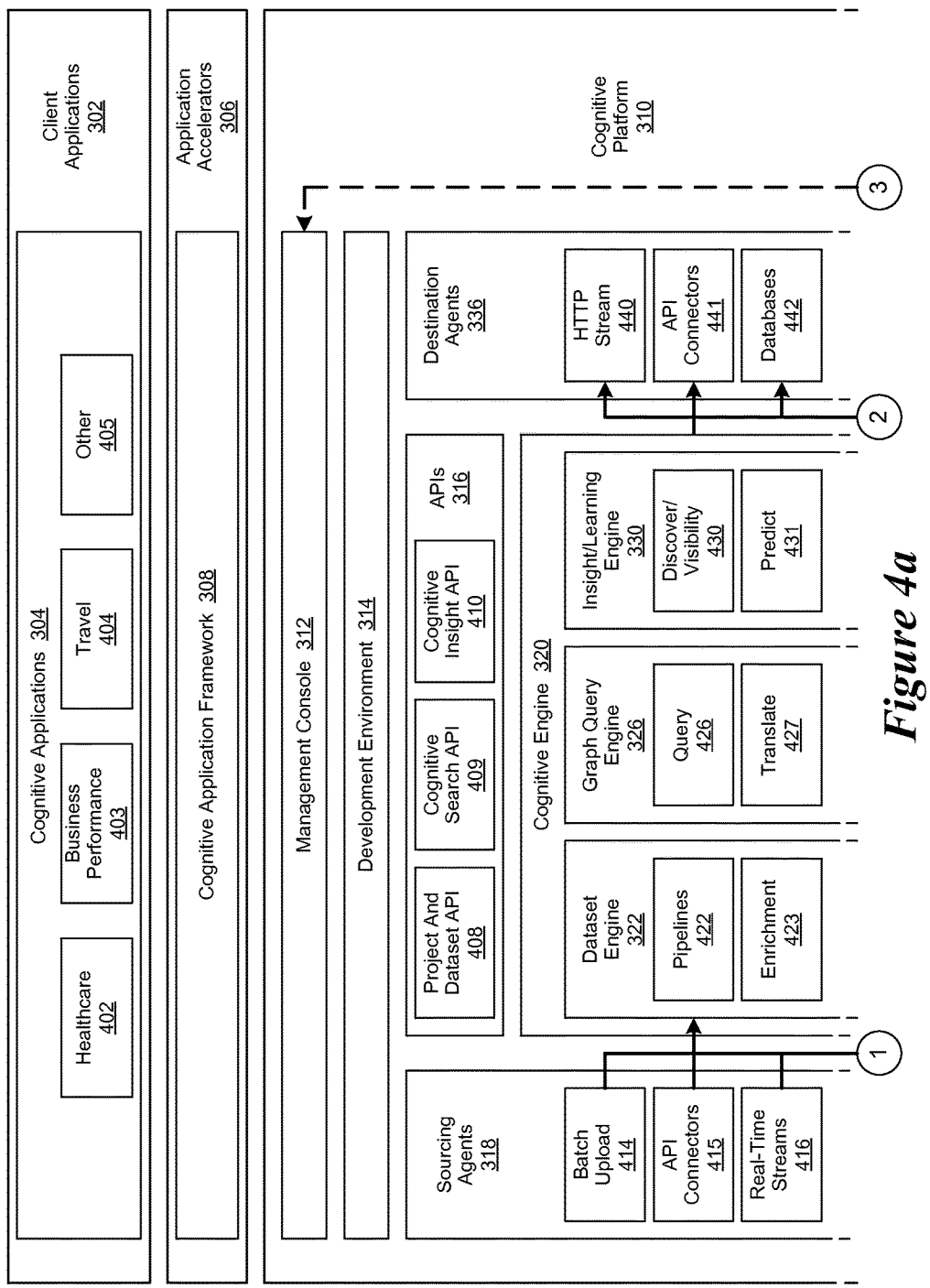
FIGS. 4a through 4c depict additional components of the CILS reference model shown in FIG. 3.
Figure 4B:
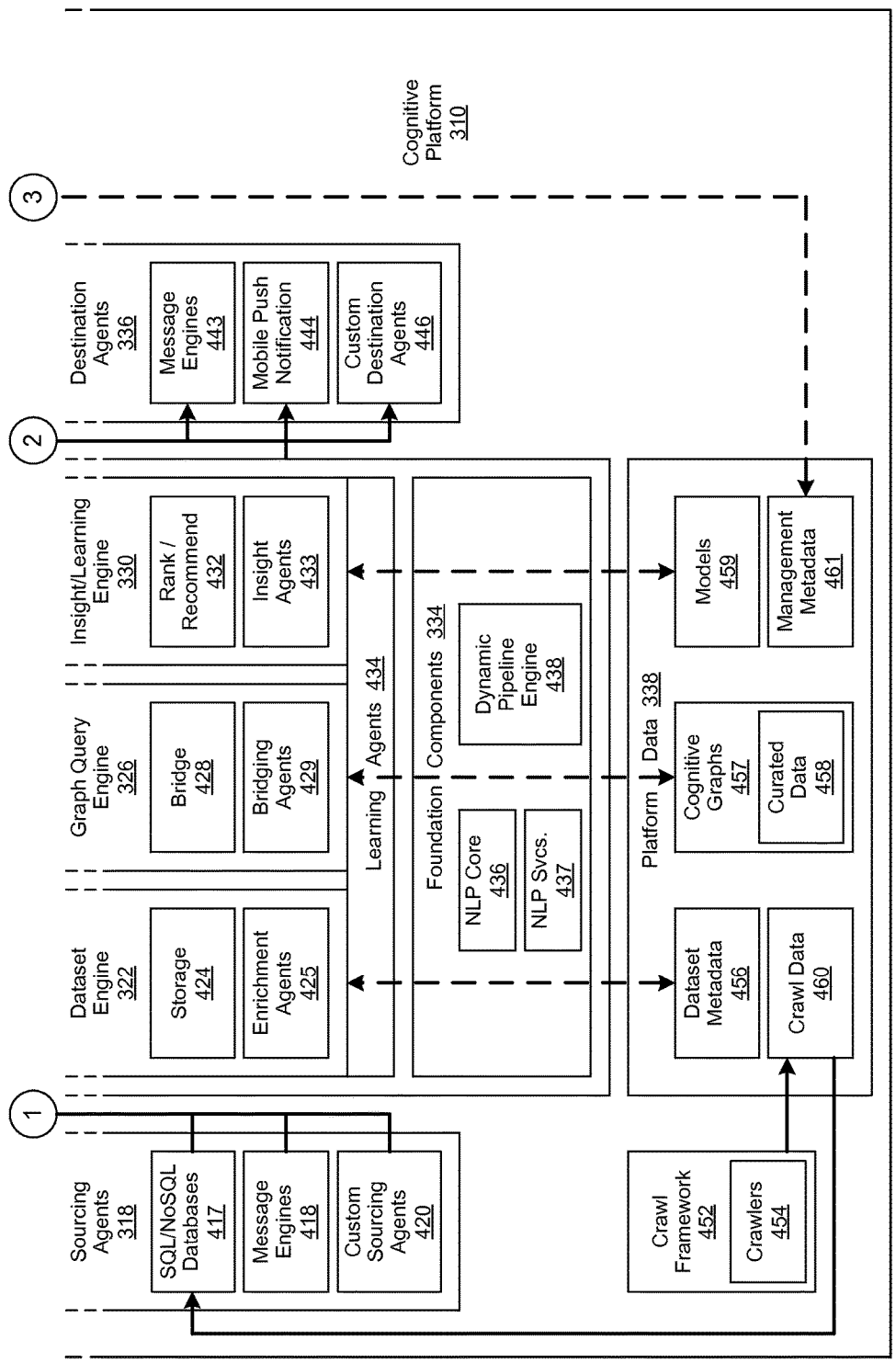
Figure 4C:
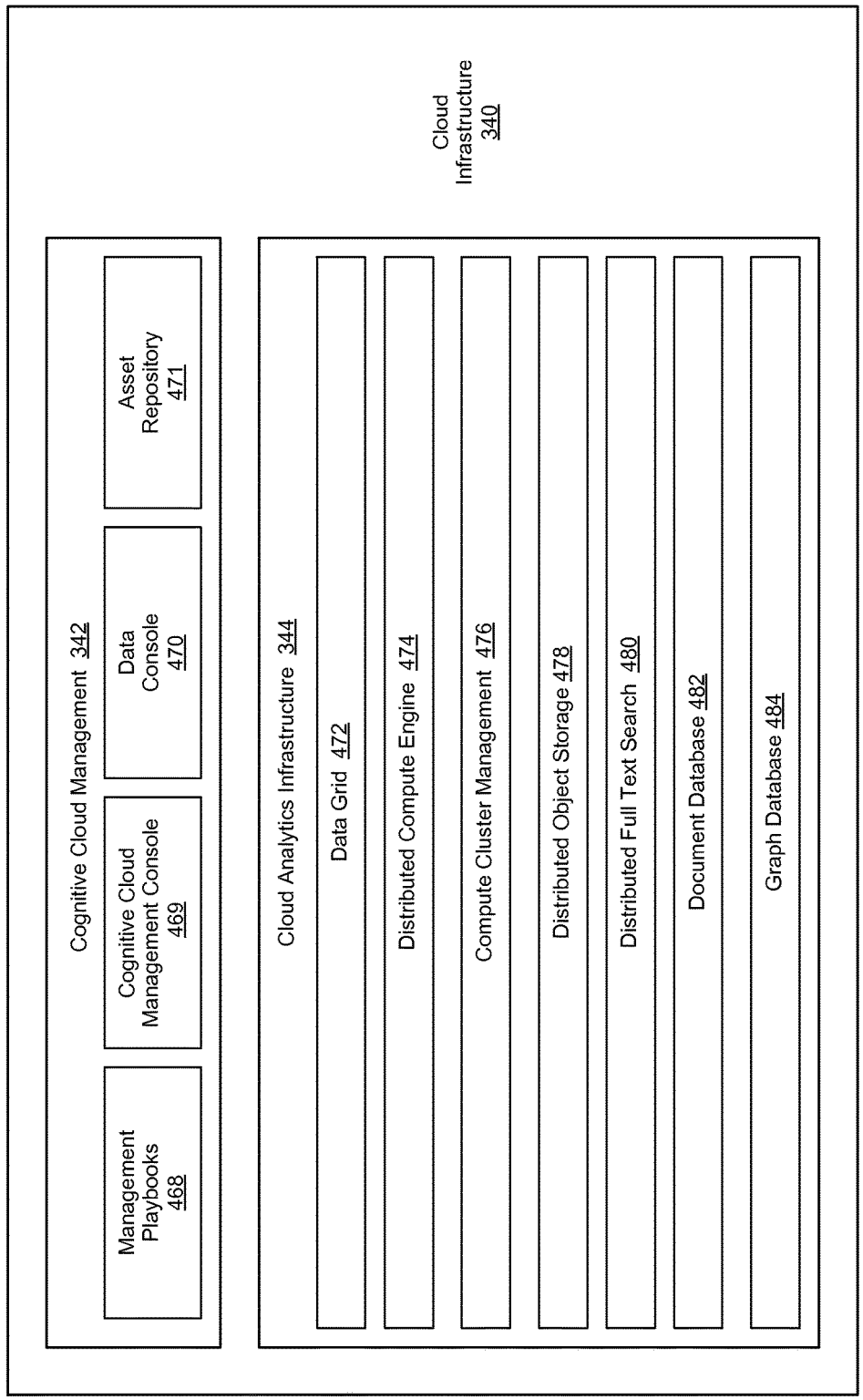

FIGS. 4a through 4c depict additional cognitive inference and learning system (CILS) components implemented in accordance with an embodiment of the CILS reference model shown in FIG. 3. In this embodiment, the CILS reference model includes client applications 302, application accelerators 306, a cognitive platform 310, and cloud infrastructure 340. As shown in FIG. 4a, the client applications 302 include cognitive applications 304. In various embodiments, the cognitive applications 304 are implemented natively accept and understand human forms of communication, such as natural language text, audio, images, video, and so forth. In certain embodiments, the cognitive applications 304 may include healthcare 402, business performance 403, travel 404, and various other 405 applications familiar to skilled practitioners of the art. As such, the foregoing is only provided as examples of such cognitive applications 304 and is not intended to limit the intent, spirit of scope of the invention.

In various embodiments, the application accelerators 306 include a cognitive application framework 308. In certain embodiments, the application accelerators 308 and the cognitive application framework 308 support various plug-ins and components that facilitate the creation of client applications 302 and cognitive applications 304. In various embodiments, the application accelerators 306 include widgets, user interface (UI) components, reports, charts, and back-end integration components familiar to those of skill in the art. It will be appreciated that many such application accelerators 306 are possible and their provided functionality, selection, provision and support are a matter of design choice. As such, the application accelerators 306 described in greater detail herein are not intended to limit the spirit, scope or intent of the invention.

As shown in FIGS. 4a and 4b, the cognitive platform 310 includes a management console 312, a development environment 314, application program interfaces (APIs) 316, sourcing agents 318, a cognitive engine 320, destination agents 336, platform data 338, and a crawl framework 452. In various embodiments, the management console 312 is implemented to manage accounts and projects, along with management metadata 461 that is used to drive processes and operations within the cognitive platform 310 for a predetermined project.

In various embodiments, the management console 312 is implemented to run various services on the cognitive platform 310. In certain embodiments, the management console 312 is implemented to manage the configuration of the cognitive platform 310. In certain embodiments, the management console 312 is implemented to establish the development environment 314. In various embodiments, the management console 312 may be implemented to manage the development environment 314 once it is established. Skilled practitioners of the art will realize that many such embodiments are possible and the foregoing is not intended to limit the spirit, scope or intent of the invention.

In various embodiments, the development environment 314 is implemented to create custom extensions to the CILS 118 shown in FIG. 2. In these and other embodiments, the development environment 314 is implemented to support various programming languages, such as Python, Java, R, and others familiar to skilled practitioners of the art. In various embodiments, the development environment 314 is implemented to allow one or more of these various programming languages to create a variety of analytic models and applications. As an example, the development environment 314 may be implemented to support the R programming language, which in turn can be used to create an analytic model that is then hosted on the cognitive platform 310.

In certain embodiments, the development environment 314 is implemented for the development of various custom applications or extensions related to the cognitive platform 310, which may subsequently be deployed in a public, private or hybrid cloud environment. In various embodiments, the development environment 314 is implemented for the development of various custom sourcing agents 318, custom enrichment agents 425, custom bridging agents 429, custom insight agents 433, custom destination agents 336, and custom learning agents 434, which are described in greater detail herein.

In various embodiments, the APIs 316 are implemented to build and manage predetermined cognitive applications 304, described in greater detail herein, which are then executed on the cognitive platform 310 to generate cognitive insights. In these embodiments, the APIs 316 may include one or more of a project and dataset API 408, a cognitive search API 409, a cognitive insight API 410, and other APIs. The selection of the individual APIs 316 implemented in various embodiments is a matter design choice and the foregoing is not intended to limit the spirit, scope or intent of the invention.

In various embodiments, the project and dataset API 408 is implemented with the management console 312 to enable the management of a variety of data and metadata associated with various cognitive insight projects and user accounts hosted or supported by the cognitive platform 310. In one embodiment, the data and metadata managed by the project and dataset API 408 are associated with billing information familiar to those of skill in the art. In one embodiment, the project and dataset API 408 is used to access a data stream that is created, configured and orchestrated, as described in greater detail herein, by the dataset engine 322.

In various embodiments, the cognitive search API 409 uses natural language processes familiar to those of skill in the art to search a target cognitive graph. Likewise, the cognitive insight API 410 is implemented in various embodiments to configure the insight/learning engine 330 to provide access to predetermined outputs from one or more cognitive graph algorithms that are executing in the cognitive platform 310. In certain embodiments, the cognitive insight API 410 is implemented to subscribe to, or request, such predetermined outputs.

In various embodiments, the sourcing agents 318 may include a batch upload 414 agent, an API connectors 415 agent, a real-time streams 416 agent, a Structured Query Language (SQL)/Not Only SQL (NoSQL) databases 417 agent, a message engines 418 agent, and one or more custom sourcing 420 agents. Skilled practitioners of the art will realize that other types of sourcing agents 318 may be used in various embodiments and the foregoing is not intended to limit the spirit, scope or intent of the invention. In various embodiments, the sourcing agents 318 are implemented to source a variety of multi-site, multi-structured source streams of data described in greater detail herein. In certain embodiments, each of the sourcing agents 318 has a corresponding API.

In various embodiments, the batch uploading 414 agent is implemented for batch uploading of data to the cognitive platform 310. In these embodiments, the uploaded data may include a single data element, a single data record or file, or a plurality of data records or files. In certain embodiments, the data may be uploaded from more than one source and the uploaded data may be in a homogenous or heterogeneous form. In various embodiments, the API connectors 415 agent is implemented to manage interactions with one or more predetermined APIs that are external to the cognitive platform 310. As an example, Associated Press® may have their own API for news stories, Expedia® for travel information, or the National Weather Service for weather information. In these examples, the API connectors 415 agent would be implemented to determine how to respectively interact with each organization's API such that the cognitive platform 310 can receive information.

In various embodiments, the real-time streams 416 agent is implemented to receive various streams of data, such as social media streams (e.g., Twitter feeds) or other data streams (e.g., device data streams). In these embodiments, the streams of data are received in near-real-time. In certain embodiments, the data streams include temporal attributes. As an example, as data is added to a blog file, it is time-stamped to create temporal data. Other examples of a temporal data stream include Twitter feeds, stock ticker streams, device location streams from a device that is tracking location, medical devices tracking a patient's vital signs, and intelligent thermostats used to improve energy efficiency for homes.

In certain embodiments, the temporal attributes define a time window, which can be correlated to various elements of data contained in the stream. For example, as a given time window changes, associated data may have a corresponding change. In various embodiments, the temporal attributes do not define a time window. As an example, a social media feed may not have predetermined time windows, yet it is still temporal. As a result, the social media feed can be processed to determine what happened in the last 24 hours, what happened in the last hour, what happened in the last 15 minutes, and then determine related subject matter that is trending.

In various embodiments, the SQL/NoSQL databases 417 agent is implemented to interact with one or more target databases familiar to those of skill in the art. For example, the target database may include a SQL, NoSQL, delimited flat file, or other form of database. In various embodiments, the message engines 418 agent is implemented to provide data to the cognitive platform 310 from one or more message engines, such as a message queue (MQ) system, a message bus, a message broker, an enterprise service bus (ESB), and so forth. Skilled practitioners of the art will realize that there are many such examples of message engines with which the message engines 418 agent may interact and the foregoing is not intended to limit the spirit, scope or intent of the invention.

In various embodiments, the custom sourcing agents 420, which are purpose-built, are developed through the use of the development environment 314, described in greater detail herein. Examples of custom sourcing agents 420 include sourcing agents for various electronic medical record (EMR) systems at various healthcare facilities. Such EMR systems typically collect a variety of healthcare information, much of it the same, yet it may be collected, stored and provided in different ways. In this example, the custom sourcing agents 420 allow the cognitive platform 310 to receive information from each disparate healthcare source.

In various embodiments, the cognitive engine 320 includes a dataset engine 322, a graph engine 326, an insight/learning engine 330, learning agents 434, and foundation components 334. In these and other embodiments, the dataset engine 322 is implemented as described in greater detail to establish and maintain a dynamic data ingestion and enrichment pipeline. In various embodiments, the dataset engine 322 may include a pipelines 422 component, an enrichment 423 component, a storage component 424, and one or more enrichment agents 425.

In various embodiments, the pipelines 422 component is implemented to ingest various data provided by the sourcing agents 318. Once ingested, this data is converted by the pipelines 422 component into streams of data for processing.

In certain embodiments, these managed streams are provided to the enrichment 423 component, which performs data enrichment operations familiar to those of skill in the art. As an example, a data stream may be sourced from Associated Press® by a sourcing agent 318 and provided to the dataset engine 322. The pipelines 422 component receives the data stream and routes it to the enrichment 423 component, which then enriches the data stream by performing sentiment analysis, geotagging, and entity detection operations to generate an enriched data stream. In certain embodiments, the enrichment operations include filtering operations familiar to skilled practitioners of the art. To further the preceding example, the Associated Press® data stream may be filtered by a predetermined geography attribute to generate an enriched data stream.

The enriched data stream is then subsequently stored, as described in greater detail herein, in a predetermined location. In various embodiments, the enriched data stream is cached by the storage 424 component to provide a local version of the enriched data stream. In certain embodiments, the cached, enriched data stream is implemented to be "replayed" by the cognitive engine 320. In one embodiment, the replaying of the cached, enriched data stream allows incremental ingestion of the enriched data stream instead of ingesting the entire enriched data stream at one time. In various embodiments, one or more enrichment agents 425 are implemented to be invoked by the enrichment component 423 to perform one or more enrichment operations described in greater detail herein.

In various embodiments, the graph query engine 326 is implemented to receive and process queries such that they can be bridged into a cognitive graph, as described in greater detail herein, through the use of a bridging agent. In these embodiments, the graph query engine may include a query 426 component, a translate 427 component, a bridge 428 component, and one or more bridging agents 429.

In various embodiments, the query 426 component is implemented to support natural language queries. In these and other embodiments, the query 426 component receives queries, processes them (e.g., using NLP processes), and then maps the processed query to a target cognitive graph. In various embodiments, the translate 427 component is implemented to convert the processed queries provided by the query 426 component into a form that can be used to query a target cognitive graph. To further differentiate the distinction between the functionality respectively provided by the query 426 and translate 427 components, the query 426 component is oriented toward understanding a query from a user. In contrast, the translate 427 component is oriented to translating a query that is understood into a form that can be used to query a cognitive graph.

In various embodiments, the bridge 428 component is implemented to generate an answer to a query provided by the translate 427 component. In certain embodiments, the bridge 428 component is implemented to provide domain-specific responses when bridging a translated query to a cognitive graph. For example, the same query bridged to a target cognitive graph by the bridge 428 component may result in different answers for different domains, dependent upon domain-specific bridging operations performed by the bridge 428 component.

To further differentiate the distinction between the translate 427 component and the bridging 428 component, the translate 427 component relates to a general domain translation of a question. In contrast, the bridging 428 component allows the question to be asked in the context of a specific domain (e.g., healthcare, travel, etc.), given what is known about the data. In certain embodiments, the bridging 428 component is implemented to process what is known about the translated query, in the context of the user, to provide an answer that is relevant to a specific domain.

As an example, a user may ask, "Where should I eat today?" If the user has been prescribed a particular health regimen, the bridging 428 component may suggest a restaurant with a "heart healthy" menu. However, if the user is a business traveler, the bridging 428 component may suggest the nearest restaurant that has the user's favorite food. In various embodiments, the bridging 428 component may provide answers, or suggestions, that are composed and ranked according to a specific domain of use. In various embodiments, the bridging agent 429 is implemented to interact with the bridging component 428 to perform bridging operations described in greater detail herein. In these embodiments, the bridging agent interprets a translated query generated by the query 426 component within a predetermined user context, and then maps it to predetermined nodes and links within a target cognitive graph.

In various embodiments, the insight/learning engine 330 is implemented to encapsulate a predetermined algorithm, which is then applied to a target cognitive graph to generate a result, such as a cognitive insight or a recommendation. In certain embodiments, one or more such algorithms may contribute to answering a specific question and provide additional cognitive insights or recommendations. In these and other embodiments, the insight/learning engine 330 is implemented to perform insight/learning operations, described in greater detail herein. In various embodiments, the insight/learning engine 330 may include a discover/visibility 430 component, a predict 431 component, a rank/recommend 432 component, and one or more insight 433 agents.

In various embodiments, the discover/visibility 430 component is implemented to provide detailed information related to a predetermined topic, such as a subject or an event, along with associated historical information. In certain embodiments, the predict 431 component is implemented to perform predictive operations to provide insight into what may next occur for a predetermined topic. In various embodiments, the rank/recommend 432 component is implemented to perform ranking and recommendation operations to provide a user prioritized recommendations associated with a provided cognitive insight.

In certain embodiments, the insight/learning engine 330 may include additional components. For example the additional components may include classification algorithms, clustering algorithms, and so forth. Skilled practitioners of the art will realize that many such additional components are possible and that the foregoing is not intended to limit the spirit, scope or intent of the invention. In various embodiments, the insights agents 433 are implemented to create a visual data story, highlighting user-specific insights, relationships and recommendations. As a result, it can share, operationalize, or track business insights in various embodiments. In various embodiments, the learning agent 434 work in the background to continually update the cognitive graph, as described in greater detail herein, from each unique interaction with data and users.

In various embodiments, the destination agents 336 are implemented to publish cognitive insights to a consumer of cognitive insight data. Examples of such consumers of cognitive insight data include target databases, business intelligence applications, and mobile applications. In various embodiments, the destination agents 336 may include a Hypertext Transfer Protocol (HTTP) stream 440 agent, an API connectors 441 agent, a databases 442 agent, a message engines 443 agent, a mobile push notification 444 agent, and one or more custom destination 446 agents. Skilled practitioners of the art will realize that other types of destination agents 318 may be used in various embodiments and the foregoing is not intended to limit the spirit, scope or intent of the invention. In certain embodiments, each of the destination agents 318 has a corresponding API.

In various embodiments, the HTTP stream 440 agent is implemented for providing various HTTP streams of cognitive insight data to a predetermined cognitive data consumer. In these embodiments, the provided HTTP streams may include various HTTP data elements familiar to those of skill in the art. In certain embodiments, the HTTP streams of data are provided in near-real-time. In various embodiments, the API connectors 441 agent is implemented to manage interactions with one or more predetermined APIs that are external to the cognitive platform 310. As an example, various target databases, business intelligence applications, and mobile applications may each have their own unique API.

In various embodiments, the databases 442 agent is implemented for provision of cognitive insight data to one or more target databases familiar to those of skill in the art. For example, the target database may include a SQL, NoSQL, delimited flat file, or other form of database. In these embodiments, the provided cognitive insight data may include a single data element, a single data record or file, or a plurality of data records or files. In certain embodiments, the data may be provided to more than one cognitive data consumer and the provided data may be in a homogenous or heterogeneous form. In various embodiments, the message engines 443 agent is implemented to provide cognitive insight data to one or more message engines, such as a message queue (MQ) system, a message bus, a message broker, an enterprise service bus (ESB), and so forth. Skilled practitioners of the art will realize that there are many such examples of message engines with which the message engines 443 agent may interact and the foregoing is not intended to limit the spirit, scope or intent of the invention.

In various embodiments, the custom destination agents 420, which are purpose-built, are developed through the use of the development environment 314, described in greater detail herein. Examples of custom destination agents 420 include destination agents for various electronic medical record (EMR) systems at various healthcare facilities. Such EMR systems typically collect a variety of healthcare information, much of it the same, yet it may be collected, stored and provided in different ways. In this example, the custom destination agents 420 allow such EMR systems to receive cognitive insight data in a form they can use.

In various embodiments, data that has been cleansed, normalized and enriched by the dataset engine, as described in greater detail herein, is provided by a destination agent 336 to a predetermined destination, likewise described in greater detail herein. In these embodiments, neither the graph query engine 326 nor the insight/learning engine 330 are implemented to perform their respective functions.

In various embodiments, the foundation components 334 are implemented to enable the dataset engine 322, the graph query engine 326, and the insight/learning engine 330 to perform their respective operations and processes. In these and other embodiments, the foundation components 334 may include an NLP core 436 component, an NLP services 437 component, and a dynamic pipeline engine 438. In various embodiments, the NLP core 436 component is implemented to provide a set of predetermined NLP components for performing various NLP operations described in greater detail herein.

In these embodiments, certain of these NLP core components are surfaced through the NLP services 437 component, while some are used as libraries. Examples of operations that are performed with such components include dependency parsing, parts-of-speech tagging, sentence pattern detection, and so forth. In various embodiments, the NLP services 437 component is implemented to provide various internal NLP services, which are used to perform entity detection, summarization, and other operations, likewise described in greater detail herein. In these embodiments, the NLP services 437 component is implemented to interact with the NLP core 436 component to provide predetermined NLP services, such as summarizing a target paragraph.

In various embodiments, the dynamic pipeline engine 438 is implemented to interact with the dataset engine 322 to perform various operations related to receiving one or more sets of data from one or more sourcing agents, apply enrichment to the data, and then provide the enriched data to a predetermined destination. In these and other embodiments, the dynamic pipeline engine 438 manages the distribution of these various operations to a predetermined compute cluster and tracks versioning of the data as it is processed across various distributed computing resources. In certain embodiments, the dynamic pipeline engine 438 is implemented to perform data sovereignty management operations to maintain sovereignty of the data.

In various embodiments, the platform data 338 includes various data repositories, described in greater detail herein, that are accessed by the cognitive platform 310 to generate cognitive insights. In these embodiments, the platform data 338 repositories may include repositories of dataset metadata 456, cognitive graphs 457, models 459, crawl data 460, and management metadata 461. In various embodiments, the dataset metadata 456 is associated with curated data 458 contained in the repository of cognitive graphs 457. In these and other embodiments, the repository of dataset metadata 456 contains dataset metadata that supports operations performed by the storage 424 component of the dataset engine 322. For example, if a Mongo® NoSQL database with ten million items is being processed, and the cognitive platform 310 fails after ingesting nine million of the items, then the dataset metadata 456 may be able to provide a checkpoint that allows ingestion to continue at the point of failure instead restarting the ingestion process.

Those of skill in the art will realize that the use of such dataset metadata 456 in various embodiments allows the dataset engine 322 to be stateful. In certain embodiments, the dataset metadata 456 allows support of versioning. For example versioning may be used to track versions of modifications made to data, such as in data enrichment processes described in greater detail herein. As another example, geotagging information may have been applied to a set of data during a first enrichment process, which creates a first version of enriched data. Adding sentiment data to the same million records during a second enrichment process creates a second version of enriched data. In this example, the dataset metadata stored in the dataset metadata 456 provides tracking of the different versions of the enriched data and the differences between the two.

In various embodiments, the repository of cognitive graphs 457 is implemented to store cognitive graphs generated, accessed, and updated by the cognitive engine 320 in the process of generating cognitive insights. In various embodiments, the repository of cognitive graphs 457 may include one or more repositories of curated data 458, described in greater detail herein. In certain embodiments, the repositories of curated data 458 includes data that has been curated by one or more users, machine operations, or a combination of the two, by performing various sourcing, filtering, and enriching operations described in greater detail herein. In these and other embodiments, the curated data 458 is ingested by the cognitive platform 310 and then processed, as likewise described in greater detail herein, to generate cognitive insights. In various embodiments, the repository of models 459 is implemented to store models that are generated, accessed, and updated by the cognitive engine 320 in the process of generating cognitive insights. As used herein, models broadly refer to machine learning models. In certain embodiments, the models include one or more statistical models.

In various embodiments, the crawl framework 452 is implemented to support various crawlers 454 familiar to skilled practitioners of the art. In certain embodiments, the crawlers 454 are custom configured for various target domains. For example, different crawlers 454 may be used for various travel forums, travel blogs, travel news and other travel sites. In various embodiments, data collected by the crawlers 454 is provided by the crawl framework 452 to the repository of crawl data 460. In these embodiments, the collected crawl data is processed and then stored in a normalized form in the repository of crawl data 460. The normalized data is then provided to SQL/NoSQL database 417 agent, which in turn provides it to the dataset engine 322. In one embodiment, the crawl database 460 is a NoSQL database, such as Mongo®.

In various embodiments, the repository of management metadata 461 is implemented to store user-specific metadata used by the management console 312 to manage accounts (e.g., billing information) and projects. In certain embodiments, the user-specific metadata stored in the repository of management metadata 461 is used by the management console 312 to drive processes and operations within the cognitive platform 310 for a predetermined project. In various embodiments, the user-specific metadata stored in the repository of management metadata 461 is used to enforce data sovereignty. It will be appreciated that many such embodiments are possible and the foregoing is not intended to limit the spirit, scope or intent of the invention.

Referring now to FIG. 4c, the cloud infrastructure 340 may include a cognitive cloud management 342 component and a cloud analytics infrastructure 344 component in various embodiments. Current examples of a cloud infrastructure 340 include Amazon Web Services (AWS®), available from Amazon.com® of Seattle, Wash., IBM® Softlayer, available from International Business Machines of Armonk, N.Y., and Nebula/Openstack, a joint project between Raskspace Hosting®, of Windcrest, Tex., and the National Aeronautics and Space Administration (NASA). In these embodiments, the cognitive cloud management 342 component may include a management playbooks 468 sub-component, a cognitive cloud management console 469 sub-component, a data console 470 sub-component, an asset repository 471 sub-component. In certain embodiments, the cognitive cloud management 342 component may include various other sub-components.

In various embodiments, the management playbooks 468 sub-component is implemented to automate the creation and management of the cloud analytics infrastructure 344 component along with various other operations and processes related to the cloud infrastructure 340. As used herein, "management playbooks" broadly refers to any set of instructions or data, such as scripts and configuration data, that is implemented by the management playbooks 468 sub-component to perform its associated operations and processes.

In various embodiments, the cognitive cloud management console 469 sub-component is implemented to provide a user visibility and management controls related to the cloud analytics infrastructure 344 component along with various other operations and processes related to the cloud infrastructure 340. In various embodiments, the data console 470 sub-component is implemented to manage platform data 338, described in greater detail herein. In various embodiments, the asset repository 471 sub-component is implemented to provide access to various cognitive cloud infrastructure assets, such as asset configurations, machine images, and cognitive insight stack configurations.

In various embodiments, the cloud analytics infrastructure 344 component may include a data grid 472 sub-component, a distributed compute engine 474 sub-component, and a compute cluster management 476 sub-component. In these embodiments, the cloud analytics infrastructure 344 component may also include a distributed object storage 478 sub-component, a distributed full text search 480 sub-component, a document database 482 sub-component, a graph database 484 sub-component, and various other sub-components. In various embodiments, the data grid 472 sub-component is implemented to provide distributed and shared memory that allows the sharing of objects across various data structures. One example of a data grid 472 sub-component is Redis, an open-source, networked, in-memory, key-value data store, with optional durability, written in ANSI C. In various embodiments, the distributed compute engine 474 sub-component is implemented to allow the cognitive platform 310 to perform various cognitive insight operations and processes in a distributed computing environment. Examples of such cognitive insight operations and processes include batch operations and streaming analytics processes.

In various embodiments, the compute cluster management 476 sub-component is implemented to manage various computing resources as a compute cluster. One such example of such a compute cluster management 476 sub-component is Mesos/Nimbus, a cluster management platform that manages distributed hardware resources into a single pool of resources that can be used by application frameworks to efficiently manage workload distribution for both batch jobs and long-running services. In various embodiments, the distributed object storage 478 sub-component is implemented to manage the physical storage and retrieval of distributed objects (e.g., binary file, image, text, etc.) in a cloud environment. Examples of a distributed object storage 478 sub-component include Amazon S3®, available from Amazon.com of Seattle, Wash., and Swift, an open source, scalable and redundant storage system.

In various embodiments, the distributed full text search 480 sub-component is implemented to perform various full text search operations familiar to those of skill in the art within a cloud environment. In various embodiments, the document database 482 sub-component is implemented to manage the physical storage and retrieval of structured data in a cloud environment. Examples of such structured data include social, public, private, and device data, as described in greater detail herein. In certain embodiments, the structured data includes data that is implemented in the JavaScript Object Notation (JSON) format. One example of a document database 482 sub-component is Mongo, an open source cross-platform document-oriented database. In various embodiments, the graph database 484 sub-component is implemented to manage the physical storage and retrieval of cognitive graphs. One example of a graph database 484 sub-component is GraphDB, an open source graph database familiar to those of skill in the art.

Figure 5:
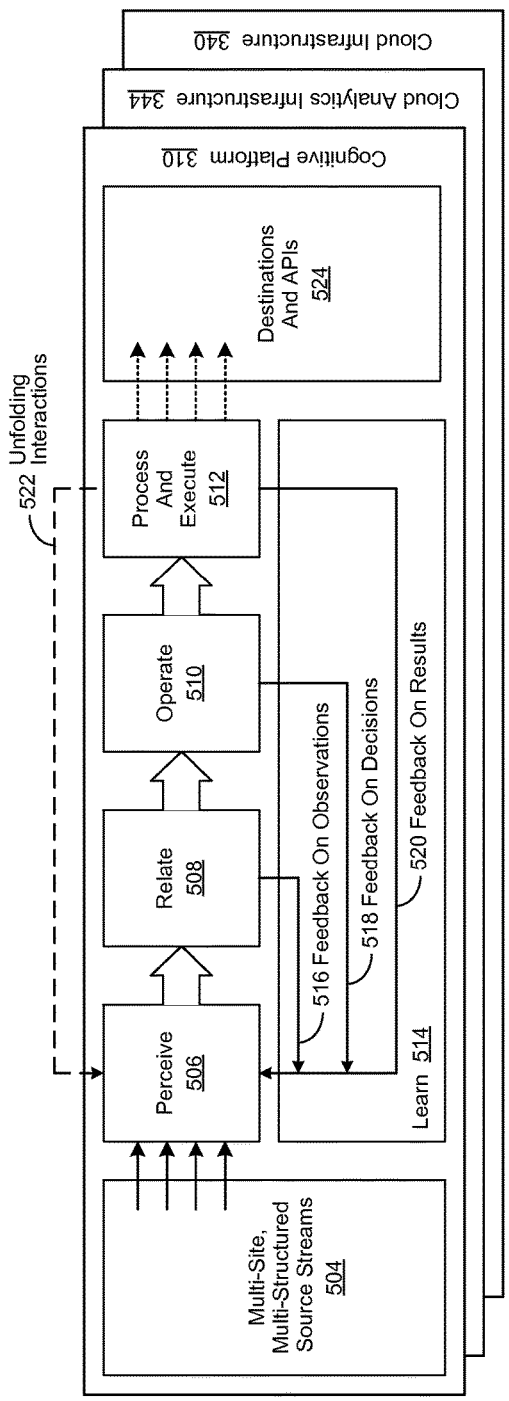
FIG. 5 is a simplified process diagram of CILS operations.

FIG. 5 is a simplified process diagram of cognitive inference and learning system (CILS) operations performed in accordance with an embodiment of the invention. In various embodiments, these CILS operations may include a perceive 506 phase, a relate 508 phase, an operate 510 phase, a process and execute 512 phase, and a learn 514 phase. In these and other embodiments, the CILS 118 shown in FIG. 2 is implemented to mimic cognitive processes associated with the human brain. In various embodiments, the CILS operations are performed through the implementation of a cognitive platform 310, described in greater detail herein. In these and other embodiments, the cognitive platform 310 may be implemented within a cloud analytics infrastructure 344, which in turn is implemented within a cloud infrastructure 340, likewise described in greater detail herein.

In various embodiments, multi-site, multi-structured source streams 504 are provided by sourcing agents, as described in greater detail herein. In these embodiments, the source streams 504 are dynamically ingested in real-time during the perceive 506 phase, and based upon a predetermined context, extraction, parsing, and tagging operations are performed on language, text and images contained in the source streams 504. Automatic feature extraction and modeling operations are then performed with the previously processed source streams 504 during the relate 508 phase to generate queries to identify related data (i.e., corpus expansion).

In various embodiments, operations are performed during the operate 510 phase to discover, summarize and prioritize various concepts, which are in turn used to generate actionable recommendations and notifications associated with predetermined plan-based optimization goals. The resulting actionable recommendations and notifications are then processed during the process and execute 512 phase to provide cognitive insights, such as recommendations, to various predetermined destinations and associated application programming interfaces (APIs) 524.

In various embodiments, features from newly-observed data are automatically extracted from user feedback during the learn 514 phase to improve various analytical models. In these embodiments, the learn 514 phase includes feedback on observations generated during the relate 508 phase, which is provided to the perceive 506 phase. Likewise, feedback on decisions resulting from operations performed during the operate 510 phase, and feedback on results resulting from operations performed during the process and execute 512 phase, are also provided to the perceive 506 phase.

In various embodiments, user interactions result from operations performed during the process and execute 512 phase. In these embodiments, data associated with the user interactions are provided to the perceive 506 phase as unfolding interactions 522, which include events that occur external to the CILS operations described in greater detail herein. As an example, a first query from a user may be submitted to the CILS system, which in turn generates a first cognitive insight, which is then provided to the user. In response, the user may respond by providing a first response, or perhaps a second query, either of which is provided in the same context as the first query. The CILS receives the first response or second query, performs various CILS operations, and provides the user a second cognitive insight. As before, the user may respond with a second response or a third query, again in the context of the first query. Once again, the CILS performs various CILS operations and provides the user a third cognitive insight, and so forth. In this example, the provision of cognitive insights to the user, and their various associated responses, results in unfolding interactions 522, which in turn result in a stateful dialog that evolves over time. Skilled practitioners of the art will likewise realize that such unfolding interactions 522, occur outside of the CILS operations performed by the cognitive platform 310.

Figure 6:
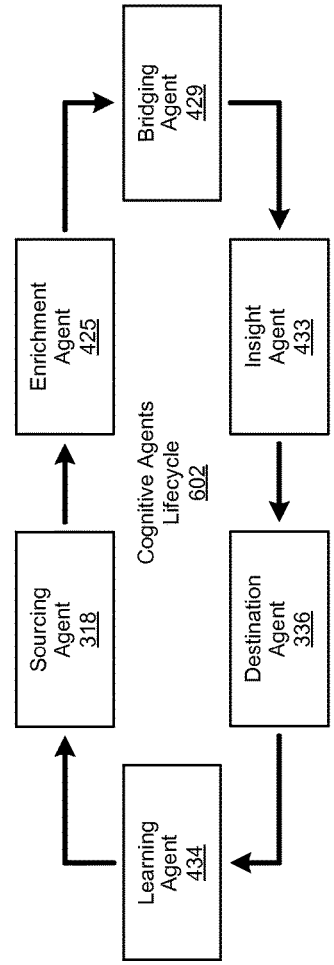
FIG. 6 is a depicts the lifecycle of CILS agents implemented to perform CILS operations.

FIG. 6 depicts the lifecycle of CILS agents implemented in accordance with an embodiment of the invention to perform CILS operations. In various embodiments, the CILS agents lifecycle 602 may include implementation of a sourcing 318 agent, an enrichment 425 agent, a bridging 429 agent, an insight 433 agent, a destination 336 agent, and a learning 434 agent. In these embodiments, the sourcing 318 agent is implemented to source a variety of multi-site, multi-structured source streams of data described in greater detail herein. These sourced data streams are then provided to an enrichment 425 agent, which then invokes an enrichment component to perform enrichment operations to generate enriched data streams, likewise described in greater detail herein.

The enriched data streams are then provided to a bridging 429 agent, which is used to perform bridging operations described in greater detail herein. In turn, the results of the bridging operations are provided to an insight 433 agent, which is implemented as described in greater detail herein to create a visual data story, highlighting user-specific insights, relationships and recommendations. The resulting visual data story is then provided to a destination 336 agent, which is implemented to publish cognitive insights to a consumer of cognitive insight data, likewise as described in greater detail herein. In response, the consumer of cognitive insight data provides feedback to a learning 434 agent, which is implemented as described in greater detail herein to provide the feedback to the sourcing agent 318, at which point the CILS agents lifecycle 602 is continued. From the foregoing, skilled practitioners of the art will recognize that each iteration of the cognitive agents lifecycle 602 provides more informed cognitive insights.

Figure 7:
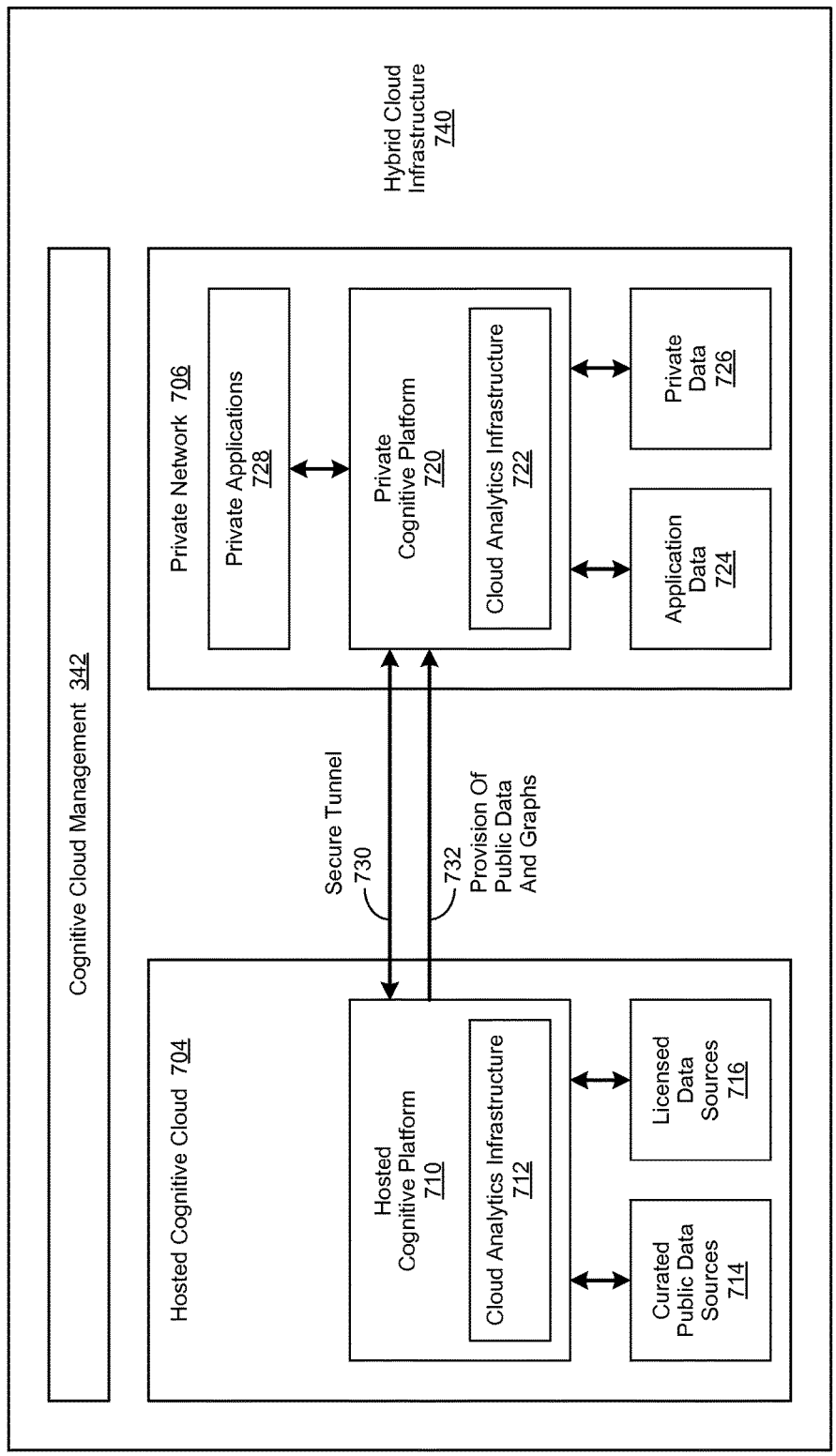
FIG. 7 is a simplified block diagram of a plurality of cognitive platforms implemented in a hybrid cloud environment.

FIG. 7 is a simplified block diagram of a plurality of cognitive platforms implemented in accordance with an embodiment of the invention within a hybrid cloud infrastructure. In this embodiment, the hybrid cloud infrastructure 740 includes a cognitive cloud management 342 component, a hosted cognitive cloud 704 environment, and a private network 706 environment. As shown in FIG. 7, the hosted cognitive cloud 704 environment includes a hosted cognitive platform 710, such as the cognitive platform 310 shown in FIGS. 3 and 4a through 4b. In various embodiments, the hosted cognitive cloud 704 environment may also include one or more repositories of curated public data sources 714 and licensed data sources 716. Likewise, the hosted cognitive platform 710 may also include a cloud analytics infrastructure 712, such as the cloud analytics infrastructure 344 shown in FIGS. 3 and 4c.

As likewise shown in FIG. 7, the private network 706 environment includes a private cognitive platform 720, such as the cognitive platform 310 shown in FIGS. 3 and 4a through 4b. In various embodiments, the private network cognitive cloud 706 environment may also include one or more repositories of application data 724 and private data 726. Likewise, the private cognitive platform 720 may also include a cloud analytics infrastructure 722, such as the cloud analytics infrastructure 344 shown in FIGS. 3 and 4c. In certain embodiments, the private network 706 environment may have one or more private applications 728 implemented to interact with the private cognitive platform 720.

In various embodiments, a secure tunnel 730, such as a virtual private network (VPN) tunnel, is implemented to allow the hosted cognitive platform 710 and the on-site cognitive platform 722 to communicate with one another. In these embodiments, the ability to communicate with one another allows the hosted cognitive platform 710 and the private cognitive platform 720 to work collaboratively when generating cognitive insights described in greater detail herein. In various embodiments, the hosted cognitive platform accesses the repositories of application data 724 and private data 726 to generate various cognitive insights, which are then provided to the private cognitive platform 720. In certain embodiments, data stored in the repositories of application data 724 and private data 726 is provided 732 to the private cognitive platform 720 in the form of public data and cognitive graphs.

In various embodiments, the private cognitive platform 720 accesses the repositories of application data 724 and private data 726 to generate various cognitive insights, which are then provided to the one or more private applications 728. In certain embodiments, the private cognitive platform 720 uses the public data and cognitive graphs provided 732 by the hosted cognitive platform 710 to generate various cognitive insights, which a then provided to the one or more private applications 728. In various embodiments, the private cognitive platform 720 accesses the repositories of application data 724 and private data 726, as well as uses the public data and cognitive graphs provided 732 by the hosted cognitive platform 710 to generate various cognitive insights. Once generated, the cognitive insights are then provided to the one or more private applications 728. Skilled practitioners of the art will recognize that many such embodiments are possible and the foregoing is not intended to limit the spirit, scope or intent of the invention.

In various embodiments, the private network 706 is implemented and managed by a travel industry entity, such as an airline, hotel chain, automobile rental company, or travel agency. In these embodiments, the private cognitive platform 720 is likewise implemented and managed by the travel industry entity to perform various cognitive insight operations relevant to travel activities. In certain embodiments, the private cognitive platform 720 is implemented to access travel-industry-specific application data 724 and private data 724 as described in greater detail herein. In these embodiments, the travel-industry-related application data 724 and private data 724 is specific to the travel industry entity. In one embodiment, the travel-industry-related application data 724 and private data 724 is private to the travel industry entity.

In various embodiments, the private network 706 is implemented and managed by a healthcare industry entity, such as hospital or healthcare management organization. In these embodiments, the private cognitive platform 720 is likewise implemented and managed by the healthcare industry entity to perform various cognitive insight operations relevant to healthcare. In certain embodiments, the private cognitive platform 720 is implemented to access healthcare-industry-specific application data 724 and private data 724 as described in greater detail herein. In these embodiments, the healthcare-industry-related application data 724 and private data 724 is specific to the healthcare industry entity.

In one embodiment, the healthcare-industry-related application data 724 and private data 724 is private to the healthcare industry entity.

Figure 8:
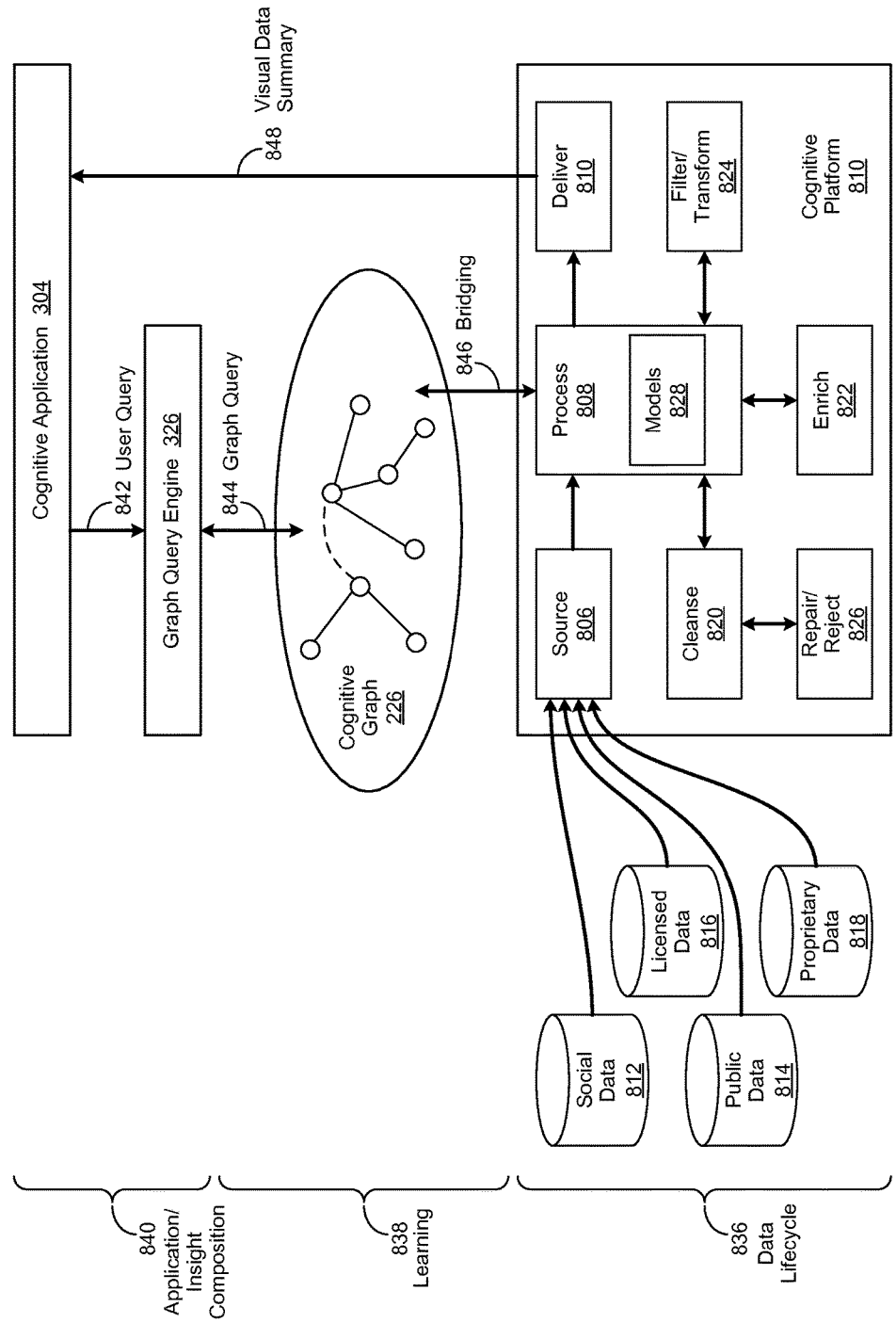
FIG. 8 is a simplified process flow diagram of a cognitive insight generation operations.

FIG. 8 is a simplified process flow diagram of a cognitive insight generation operations performed in accordance with an embodiment of the invention. In various embodiments, cognitive insight operations may be performed in various phases. In this embodiment, these phases include a data lifecycle 840 phase, a learning 838 phase, and an application/insight composition 840 phase.

In the data lifecycle 836 phase, a predetermined cognitive platform 810 instantiation sources social data 812, public data, licensed data 816, and proprietary data 818 from various sources as described in greater detail herein. In various embodiments, an example of a cognitive platform 810 instantiation is the cognitive platform 310 shown in FIGS. 3 and 4a through 4b. In this embodiment, the cognitive platform 810 instantiation includes a source 806 component, a process 808 component, a deliver 810 component, a cleanse 820 component, an enrich 822 component, a filter/transform 824 component, and a repair/reject 826 component. Likewise, as shown in FIG. 8, the process 808 component includes a repository of models 828, described in greater detail herein.

In various embodiments, the process 806 component is implemented to perform various cognitive insight generation and other processing operations, described in greater detail herein. In these embodiments, the process component is implemented to interact with the source 806 component, which in turn is implemented to perform various data sourcing operations described in greater detail herein. In various embodiments, the sourcing operations are performed by one or more sourcing agents, as likewise described in greater detail herein. The resulting sourced data is then provided to the process 808 component. In turn, the process 808 component is implemented to interact with the cleanse 820 component, which is implemented to perform various data cleansing operations familiar to those of skill in the art. As an example, the cleanse 820 component may perform data normalization or pruning operations, likewise known to skilled practitioners of the art. In certain embodiments, the cleanse 820 component may be implemented to interact with the repair/reject 826 component, which in turn is implemented to perform various data repair or data rejection operations known to those of skill in the art.

Once data cleansing, repair and rejection operations are completed, the process 808 component is implemented to interact with the enrich 822 component, which is implemented to perform various data enrichment operations described in greater detail herein. Once data enrichment operations have been completed, the process 808 component is likewise implemented to interact with the filter/transform 824, which in turn is implemented to perform data filtering and transformation operations described in greater detail.

In various embodiments, the process 808 component is implemented to generate various models, described in greater detail herein, which are stored in the repository of models 828. The process 808 component is likewise implemented in various embodiments use the sourced data to generate one or more cognitive graphs 226, as described in greater detail herein. In various embodiments, the process 808 component is implemented to gain an understanding of the data sourced from the sources of social data 812, public data, licensed data 816, and proprietary data 818, which assist in the automated generation of the cognitive graph 226.

The process 808 component is likewise implemented in various embodiments to perform bridging 846 operations, likewise described in greater detail, to access the cognitive graph 226. In certain embodiments, the bridging 846 operations are performed by bridging agents, as described in greater detail herein. In various embodiments, the cognitive graph 226 is accessed by the process 808 component during the learning 836 phase of the cognitive insight generation operations.

In various embodiments, a cognitive application 304 is implemented to receive user input, such as a user query 842, which is then submitted during the application/insight composition 840 phase to a graph query engine 326. In turn, the graph query engine 326 processes the user query 842 to generate a graph query 844, as described in greater detail herein. The graph query 844 is then used to query the cognitive graph 226, which results in the generation of one or more cognitive insights. In various embodiments, the process 808 component is implemented to provide these cognitive insights to the deliver 810, which in turn is implemented to deliver the cognitive insights in the form of a visual data summary 848 to the cognitive application 304. In various embodiments, as described in the descriptive text associated with FIG. 5, learning operations are iteratively performed during the learning 838 phase to provide more accurate and useful cognitive insights.

In various embodiments, the cognitive insight generation operations are performed to generate travel-relevant cognitive insights. In these embodiments the social data 812, public data, licensed data 816, and proprietary data 818 sourced from various sources may contain travel-relevant data. For example, the licensed data 816 may be ticket sale information from Sojurn®, weather data from Weather Underground®, Weather.com®, and so forth. Likewise, public data 814 may be Department of Transportation (DOT), Bureau of Transportation Services (BTS), of on-time arrival information provided by various airlines. Proprietary data 818 may likewise include data privately-owned data, such as an airline's frequent flier information that is only used internally to the airline.

As described in greater detail herein, the cognitive platform 810 instantiation is implemented in these embodiments to process this travel-relevant data, and other associated data, to generate travel-relevant cognitive insights. As an example, a user may provide a travel-relevant user query 842 to a travel website, such as TripAdvisor.com. In this example, the cognitive insight generation operations are performed to provide an enhanced cognitive search of the travel-relevant website to find a preferred destination, for a specific time frame, for the user. To extend the example, the travel-relevant user query 842 may not be in the form of a traditional query. Instead, the user may submit a statement, such as, "I want to go on a vacation with my family, to the beach, in Florida, in July." or possibly, "I want to go to Utah in May on a mountain biking trip." To extend the example further, the user may also state, "I want to use my frequent flier miles for airline travel and my awards program points for my accommodations."

In various embodiments, a user query 842 that includes such statements is processed by the graph query engine 326 to generate one or more travel-relevant graph queries 844. In these embodiments, these travel-relevant graph queries 844 are implemented to understand concepts like destinations, travel-related activities, and purpose of travel. Examples of such concepts include the difference between a honeymoon and a business trip, time frames that are related to travel (e.g., flight segments, time zones, etc.), and various recreational venues.

The resulting graph queries 844 are then used to query a travel-relevant instantiation of the cognitive graph 226, which in turn results in the generation of one or more travel-relevant cognitive insights. In certain of these embodiments, the cognitive graph 226 contains travel-relevant data, such as locations, hotels, prices, promotions, and so forth. In various embodiments, the deliver 810 component is implemented to provide the travel-relevant cognitive insights in the form of a visual data summary 848. As an example, the visual data summary 848 may be provided to the user as a travel review. In various embodiments, the visual data summary 848 may be provided to a predetermined destination associated with the user. In these embodiments, the destination may be a mobile application, an alert, a business intelligence application, a statistical tool, a third party application, a marketplace, or an application program interface (API).

Although the present invention has been described in detail, it should be understood that various changes, substitutions and alterations can be made hereto without departing from the spirit and scope of the invention as defined by the appended claims.

What is claimed is:

1. A method for providing healthcare optimized cognitive insights comprising:
   receiving data from a plurality of data sources, at least some of the plurality of data sources comprising healthcare relevant data sources, the plurality of data sources comprising a social data source stored in a social data repository, the social data comprising data from social media feeds, a public data source stored in a public data repository, a licensed data source stored in a licensed data repository and a private data source stored in a private data repository, the private data source comprising healthcare company private data, the private data repository being maintained within a private network environment;
   processing the data from the plurality of data sources to provide cognitively processed insights, the processing being performed by a cognitive inference and learning system, the cognitive inference and learning system comprising a private cognitive platform executing on a hardware processor of an information processing system within the private network environment, the private cognitive platform and the information processing system performing a cognitive computing function, the private cognitive platform comprising a private cognitive engine;
   performing a learning operation via the private cognitive engine to iteratively improve the cognitively processed insights over time; and,
   providing the cognitively processed healthcare relevant insights to a destination via a cognitive insight stream, the cognitive insight stream comprising a stream of visualized insights, the destination comprising a private cognitive application, the private cognitive application enabling a user to interact with the cognitively processed healthcare relevant cognitive insights via a user interface.

2. The method of claim 1, wherein:
   the plurality of data sources comprise at least one of situational data sources and temporal data sources, the situational data sources comprising a healthcare related situational data source, the temporal data sources comprising a healthcare related temporal data source.

3. The method of claim 1, wherein:
the plurality of data sources comprise at least one of a social data source, a public data source, a private data source and device data source, the private data source comprising healthcare company private data.

4. The method of claim 1, further comprising:
performing analysis operations to achieve a semantic level of understanding about language by relating syntactic structures.

5. The method of claim 1, further comprising:
performing multi-criteria decision making operations to achieve a goal.

6. The method of claim 1, further comprising:
filtering for information through collaborative involvement of a plurality of entities.

7. The method of claim 1, further comprising:
inherently making deductions from commonly known facts.

8. The method of claim 1, further comprising:
enabling natural language interactions with the cognitive inference and learning system.

9. The method of claim 1, further comprising:
processing information, organizing the information, ranking the information and generating a corresponding summary of the information.

10. The method of claim 1, further comprising:
reasoning based upon qualitative abstractions of temporal and spatial aspects of common sense knowledge.

11. The method of claim 1, further comprising:
identifying elements in a set of data that refer to the same entity across different data sources.

12. The cognitive information processing system environment of claim 1, wherein:
the destination comprises at least one of a mobile application, an alert, a business intelligence type application, a statistical tool, a third party custom application, a marketplace and an application program interface.

13. A method for providing healthcare optimized cognitive insights comprising:
receiving data from a plurality of data sources, at least some of the plurality of data sources comprising healthcare relevant data sources, the plurality of data sources comprising a social data source stored in a social data repository, public data source stored in a public data repository, licensed data source stored in a licensed data repository and a private data source stored in a private data repository, the private data source comprising healthcare company private data, the private data repository being maintained within a private network environment;
processing the data from the plurality of data sources to provide cognitively processed insights, the processing being performed by a cognitive inference and learning system coupled to receive data from the plurality of data sources, the cognitive inference and learning system executing on a hardware processor of an information processing system, the cognitive inference and learning system processing the data from the plurality of data sources to provide cognitively processed healthcare relevant insights, the cognitive inference and learning system comprising a private cognitive platform executing within the private network environment, the private cognitive platform comprising
a cognitive engine, the cognitive engine comprising a dataset engine, a graph query engine and an insight/learning engine,
a plurality of sourcing agents, the plurality of sourcing agents sourcing a variety of multi-site, multi-structured data streams,
a plurality of destination agents, the plurality of destination agents publishing the cognitively processed healthcare relevant insights to a consumer of cognitive insight data; and,
performing, via the cognitive inference and learning system, a learning operation to iteratively improve the cognitively processed healthcare relevant insights over time; and,
providing the cognitively processed healthcare relevant insights to a destination, the destination receiving the cognitively processed healthcare relevant insights via a cognitive insight stream, the cognitive insight stream comprising a stream of visualized insights, the destination comprising a cognitive application, the cognitive application enabling a user to interact with the cognitive insights, the cognitive application comprising the consumer of the cognitive insight data.

* * * * *